US009122373B1

(12) United States Patent
Nacey

(10) Patent No.: US 9,122,373 B1
(45) Date of Patent: Sep. 1, 2015

(54) VISUAL DISPLAY OF ROOM INFORMATION

(71) Applicant: TeleTracking Technologies, Inc., Pittsburgh, PA (US)

(72) Inventor: Gene E. Nacey, Leechburg, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

(21) Appl. No.: 14/052,092

(22) Filed: Oct. 11, 2013

Related U.S. Application Data

(62) Division of application No. 09/567,897, filed on May 10, 2000, now Pat. No. 8,560,580.

(60) Provisional application No. 60/133,524, filed on May 10, 1999.

(51) Int. Cl.
*G06F 17/30* (2006.01)
*G06F 3/0481* (2013.01)
*G06F 21/31* (2013.01)

(52) U.S. Cl.
CPC ............ *G06F 3/04817* (2013.01); *G06F 21/31* (2013.01)

(58) Field of Classification Search
USPC .................. 707/607, 687, 609, 821, 705, 953
See application file for complete search history.

(56) References Cited

U.S. PATENT DOCUMENTS

| 4,994,908 | A | | 2/1991 | Kuban et al. |
|---|---|---|---|---|
| 5,331,549 | A | | 7/1994 | Crawford, Jr. |
| 5,404,291 | A | | 4/1995 | Kerr et al. |
| 5,463,546 | A | * | 10/1995 | Parkhurst ........................ 705/5 |
| 5,581,461 | A | | 12/1996 | Coll et al. |
| 5,699,038 | A | | 12/1997 | Ulrich et al. |
| 5,724,065 | A | | 3/1998 | Chang et al. |
| 5,822,544 | A | * | 10/1998 | Chaco et al. ....................... 705/2 |
| 5,867,821 | A | | 2/1999 | Ballantyne et al. |
| 5,909,668 | A | | 6/1999 | Fukuma |
| 6,047,259 | A | | 4/2000 | Campbell et al. |
| 6,079,863 | A | | 6/2000 | Furukawa et al. |
| 6,566,833 | B2 | | 5/2003 | Bartlett |
| 6,633,900 | B1 | | 10/2003 | Khalessi et al. |
| 6,731,311 | B2 | | 5/2004 | Bufe et al. |
| 7,756,723 | B2 | | 7/2010 | Rosow et al. |
| 2002/0158919 | A1 | | 10/2002 | Nacey |
| 2003/0074222 | A1 | | 4/2003 | Rosow et al. |

FOREIGN PATENT DOCUMENTS

GB        1413324  A1    11/1975

OTHER PUBLICATIONS

Cruz, a. M., et al., "Technology management system aided by computers in a Hospitality Information System", Engineering in Medicine and Biology Society, 2000, Proceedings of the 22nd Annual International Conference of the IEEE, Jul. 23-28, 2000, Chicago, Illinois.
Microsoft Press, Microsoft Computer Dictionary, Fifth Edition, 2002, p. 91.

* cited by examiner

*Primary Examiner* — Sana Al Hashemi
(74) *Attorney, Agent, or Firm* — Ference & Associates LLC

(57) ABSTRACT

Information of interest is graphically displayed in a manner which conveys the information to in a form which aids in comprehension of the information. Specifically, the information is preferably conveyed on the unit level through the use of the unit's floor plan in a graphical seating chart type format. A graphical icon is used to represent each room in the unit. Components of the icon indicate key considerations for every room. Additional information may also be displayed by clicking on a component of the icon.

13 Claims, 2 Drawing Sheets

VISUAL DISPLAY OF ROOM INFORMATION

CROSS-REFERENCE TO RELATED APPLICATIONS

This application is a divisional of co-pending U.S. patent application Ser. No. 09/567,897, entitled "VISUAL DISPLAY OF ROOM INFORMATION", filed on May 10, 2000, which in turn claims the benefit of U.S. Provisional Application Ser. No. 60/133,524 filed on May 10, 1999; each prior application is hereby incorporated by reference.

FIELD

The present invention relates generally to a hospital communication system, and more particularly to an apparatus and method to present patient room information to hospital personnel to enhance comprehension of such information.

BACKGROUND

Nurses and other attending staff in a hospital ward or hospital wing work under conditions involving high pressure, stress and long hours. These care givers must remain alert to respond to patient needs, in both emergency and non-emergency situations. Due to economic practicalities and the ever-increasing costs of medical care, it is necessary to make the most efficient use of nurses and staff on call in a hospital ward or hospital wing, particularly at night when nurse and staff levels are maintained at a minimum.

On the other hand, a desire to optimize the efficiency of nurse and staff personnel is of secondary importance relative to the primary objective, that of providing a high level of medical care to a patient. If nurse and staff levels are reduced for the sake of efficiency without any corresponding simplification of duties and responsibilities, the level of patient care will decrease. Therefore, it is desirable to maximize the efficiency of nurses and staff on call in a hospital wing or hospital ward, but to do so in a manner which does not increase the work load or stress levels of these professional care givers nor decrease the level of patient care.

One approach to maximizing the efficiency of nurses and other hospital staff involves providing information needed by these professionals in a location remote from a patient room. For instance, U.S. Pat. No. 5,699,038 to Ulrich et al. discloses a bed status information system of hospital beds which provides remote instantaneous retrieval of unique identification information about the bed and provides status information related to the position of the bed, the configuration of the mattress surface, the status of the safety systems on the bed, and the current state of various patient care systems integrated with the bed. Monitoring of patient information therefore does not require attendance within the room to locally view and interpret various types of information. U.S. Pat. No. 5,867,821 to Ballantyne et al. discloses a method and apparatus for electronically accessing and distributing personal health care information and services in hospitals and homes in which certain information, ranging from patient health record information to patient and operating room monitoring information, is distributed to a nursing station within a hospital.

Providing information to nurses and other hospital staff in a location remote from a patient room creates certain problems. Among the problems is presenting information to the medical professionals in a way that assists them in effectively monitoring the information without increasing their level of stress, which may occur if they feel overwhelmed by the amount of information. A need has thus been recognized in conjunction with responding to the aforementioned problems.

SUMMARY

The present invention, in accordance with at least one presently preferred embodiment, utilizes the capabilities of computer to graphically display selected information in a manner which conveys the information to the nurses and other hospital staff in a form which aids in comprehension of the information. Specifically, the information is preferably conveyed on the patient unit level through the use of the patient unit's floor plan in a graphical seating chart type format. A graphical icon is used to represent each room in the patient unit. Components of the icon indicate key considerations for every bed control or admitting department. Additional information may also be displayed by clicking a component of an icon.

Consequently, the present invention broadly contemplates a method whereby hospital room information is visually displayed, thereby aiding nurses and other hospital staff in comprehending the hospital bed information. An example of other hospital staff which could benefit from the present invention include the staff in the admissions department and who assign patients to rooms.

In one aspect, the present invention provides an apparatus for the graphical display of room information, the apparatus comprising: a display and an arrangement for producing an icon for being viewed on the display, the icon conveying information on a room.

In another aspect, the present invention provides an apparatus for the graphical display of room information, the apparatus comprising: a display, an arrangement for producing an icon for being viewed on the display, the icon having a plurality of modifiable attributes, and a controller which modifies at least one of the attributes of the icon to convey information about the current status of a room.

In another aspect, the present invention provides a method of graphically displaying room information, the method comprising the steps of: displaying a floor plan of at least one room, displaying at least one icons within said floor plan, each icon corresponding to a room and having a plurality of modifiable attributes, and modifying the attributes of the icon to convey information about the current status of the room.

In an additional aspect, the present invention provides a program storage device readable by machine, tangibly embodying a program of instructions executable by the machine to perform method steps for the visual presentation of information about the status of rooms, the method comprising the steps of: displaying a floor plan of at least one room, displaying at least one icon within the floor plan, each icon corresponding to a room and having a plurality of modifiable attributes, and modifying at least one of the attributes of the icon to convey information about the current status of the room.

For a better understanding of the present invention, together with other and further features and advantages thereof, reference is made to the following description, taken in conjunction with the accompanying drawings, and the scope of the invention will be pointed out in the appended claims.

DETAILED DESCRIPTION

Figure 1:
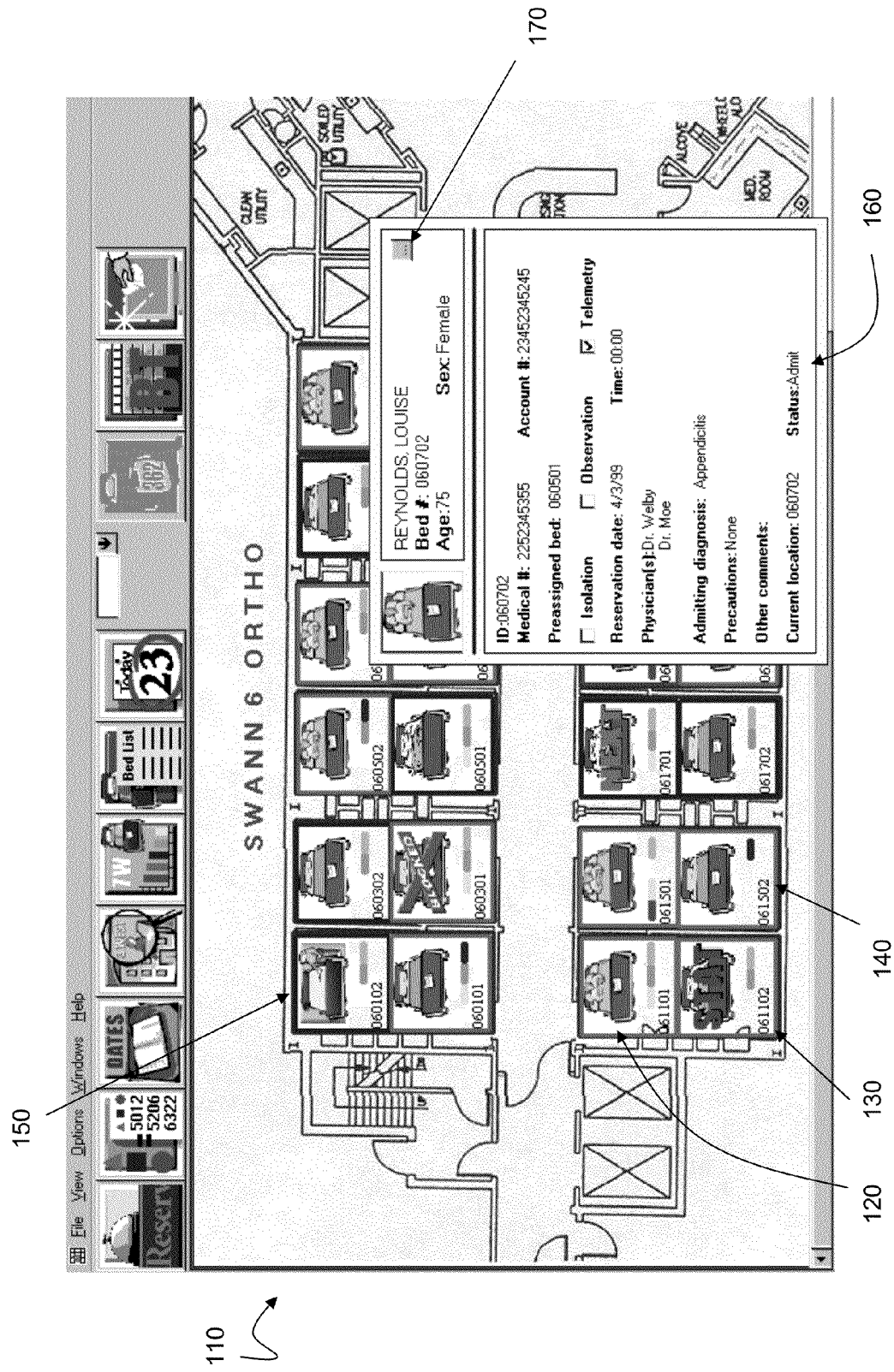
FIG. 1 illustrates a graphical depiction of a patient unit in accordance with an embodiment of the present invention.

As shown in FIG. 1, the floor plan 110 of a patient unit within a hospital is shown. An icon visually depicts the status of each room of the patient unit. The preferred components of the icon will be discussed below. To provide an example of the scope of information which is displayed in floor plan 110, however, several of the icons shown in floor plan 110 will now be generally discussed. The icon at reference numeral 120 depicts an occupied room; the icon at reference numeral 130 depicts a room in which an emergency condition exists; the icon at reference numeral 140 depicts an unoccupied room; and the icon at reference numeral 150 depicts a room being cleaned. Important information is thereby visually conveyed to the nurses and other hospital staff in a manner which assists in the comprehension of the information.

Typically, there is additional information which is useful for the nurses or other hospital staff to have and which is not as important as the information shown by the icon itself. Secondary information of this type may be displayed to nurses or other hospital staff upon clicking on an icon. It should be understood that the secondary information displayed may depend on the information conveyed by the icon itself.

By way of example, if a user were to click on icon 120, which conveys the room is occupied by a patient, secondary information such as the patient's pre-admission data may appear in a pop-up window as shown at reference numeral 160. Additional secondary information about this patient may displayed by clicking on the button 170. If the additional secondary information chosen to be made available this way is considered by the hospital or other institution to be sensitive, it is conceivable to make the information available only to those who enter a proper security identification into the system. Examples of such additional secondary information may include the patient's home address, telephone number, and social security number, although any information which an institution considers to be sensitive may be protected in this manner. Any number of layers of additional or secondary information may be made available or protected in this manner and a layer is not limited to those icons which convey the room is occupied. A layer of additional or secondary information should be understood to refer to any information which is not conveyed by the icon itself. Typically, another layer of information is obtained by clicking on the icon itself or the preceding layer.

The types of additional or secondary information which may be displayed for icons conveying information other than a room is occupied will now be discussed. By way of example, if a user were to click on icon 130, which conveys that an emergency condition exists in the room, the user could preferably be given additional information regarding the nature of the emergency condition. If a user were to click on icon 140, which conveys the room is not occupied, the user would be given additional information which could preferably include whether the room had been reserved for an incoming patient. If a user would click on icon 150, which conveys the room is being cleaned, the user could be given additional information which would preferably include the name of employee performing the cleaning and the time cleaning was commenced. It should be understood that the secondary information displayed is preferably dependent upon, and thus is appropriate for, the information visually conveyed by the icon itself. Moreover, an icon is not limited to visually conveying the information discussed in the examples herein.

Figure 2:
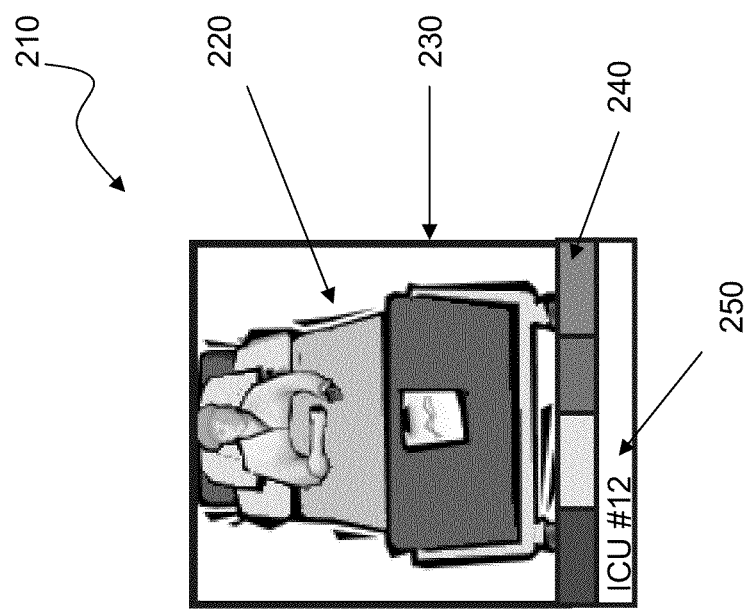
FIG. 2 illustrates a graphical icon in accordance with an embodiment of the present invention.

Referring now to FIG. 2, an icon 210 with its preferred components is shown. The portion of the icon depicted by reference numeral 220 preferably identifies the status of the bed or beds within the patient room. For icon 210, portion 220 corresponds to the bed in the corresponding room to be occupied. Accordingly, this portion 220 of the icon corresponds to the icon represented by reference numeral 120 in FIG. 1. The outer border of the icon is represented by reference numeral 230. Preferably, the color of outer border 230 depicts the sex of the patient. Blue preferably depicts a male patient and pink preferably depicts a female patient. The portion of the icon depicted by reference numeral 240 preferably contains various descriptive parameters. Although any number of descriptive parameters may be displayed in this portion of the icon, it is preferred to display four parameters to ensure the capability of viewing a significant number of parameters without excessively crowding information into the icon. Each parameter to be displayed is associated with a particular color and if the parameter applies, the corresponding color is appears in this area. Preferably, the parameters to be displayed and their associated colors are red for isolation, yellow for observation, green for telemetry, and a color indicating the age bracket of the patient, for example, light blue for an adult and brown for a child. It should be understood that the parameters to be displayed and their corresponding colors may be freely selected by an institution utilizing the system of the present invention.

It should be understood that information may be visually displayed in accordance with the present invention on a typical CRT computer monitor. It may be advantageous, however, to display such visual information on a flat panel monitor to enhance positioning of the monitor to enable a greater number of personnel to view the visual information. It should be further understood that information may be simultaneously visually displayed in accordance with the present invention for more than one patient unit. For example, it may be desirable for administrative purposes to have information for more than patient unit displayed on a single monitor screen, such as having patient units from different floors displayed on a single monitor screen. Accordingly, an administrator could view all patient units with a similar focus, for example, all cardiac units.

In recapitulation, the present invention, in accordance with at least one presently preferred embodiment, provides a manner of visually displaying information in a manner to enhance comprehension of the information. As such, it is to be understood that the present invention, in accordance with at least one presently preferred embodiment, may be utilized in environments other than hospitals, such as hotels, dorms, or any other situation where information about rooms is desired to be graphically displayed.

It is to be understood that the present invention, in accordance with at least one presently preferred embodiment, includes a display and an arrangement for producing an icon for being viewed on the display, the icon conveying information on a room. Together, these may be implemented on at least one general-purpose computer running suitable software programs. These may also be implemented on at least one Integrated Circuit or part of at least one Integrated Circuit. Thus, it is to be understood that the invention may be implemented in hardware, software, or a combination of both.

If not otherwise stated herein, it is to be assumed that all patents, patent applications, patent publications and other publications mentioned and cited herein are hereby fully incorporated by reference herein as if set forth in their entirety herein.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method of graphically displaying bed management and room occupant status information of a facility, said method comprising the steps of:
   displaying at least one icon on an interactive, display, said at least one icon simultaneously conveying a first level of hospital room information regarding: bed management information, including at least one of patient bed occupancy and bed availability, said at least one icon being arranged on said display on said display in the pattern of a floor plan of the facility;
   each of said at least one icon in said floor plan corresponding to a different one of said rooms of said facility for which information is conveyed;
   providing a link to secondary patient information in said at least one icon when said at least one icon is an icon of a patient occupied room; and
   displaying secondary patient information associated with at least one attribute of an icon in response to user interaction with the icon of a patient occupied room.

2. A program storage device readable by machine, embodying a program of instructions executable by the machine to perform steps for the graphical display of bed management and room occupant status information of a facility, said steps comprising:
   displaying at least one icon on an interactive display, said icon simultaneously conveying a first level of hospital room information regarding: bed management information, including at least one of patient bed occupancy and bed availability, said at least one icon being arranged in the pattern of a floor plan of the facility;
   each of said at least one icon in said floor plan corresponding to a different one of said rooms of said facility for which information is conveyed;
   providing a link to secondary patient information in said at least one icon when said at least one icon is an icon of a patient occupied room;
   displaying secondary patient information associated with at least one attribute of the an icon in response to user interaction with the icon of a patient occupied room.

3. The method according to claim 1, wherein the display of said secondary information is restricted.

4. The method according to claim 1, wherein the room is a hospital room.

5. The method according to claim 1, wherein an icon depicts a bed.

6. The method according to claim 1, wherein an icon indicates a room is unoccupied.

7. The method according to claim 1, wherein an icon indicates a room is occupied.

8. The method according to claim 1, wherein an icon indicates an emergency condition exists within a room.

9. The method according to claim 1, wherein an icon indicates a bed within a room is being made.

10. The method according to claim 1, wherein an icon conveys information about a room comprising a first level of hospital room information regarding patient bed occupancy and bed availability.

11. The method of claim 10, wherein the displaying secondary patient information comprises providing patient specific information in response to user interaction with an icon.

12. The method according to claim 3, wherein the secondary information is displayed solely to authorized users.

13. The method according to claim 12, wherein the authorization of a user is determined by comparing a password provided by the user against a databank of passwords.

* * * * *